(12) United States Patent
Yu

(10) Patent No.: US 7,100,611 B2
(45) Date of Patent: Sep. 5, 2006

(54) FACE MASK

(75) Inventor: Chu-Yih Yu, Taipei Hsien (TW)

(73) Assignee: Mesure Technology Co., Ltd., Taipei Hsien (TW)

( * ) Notice: Subject to any disclaimer, the term of this patent is extended or adjusted under 35 U.S.C. 154(b) by 0 days.

(21) Appl. No.: 11/136,275

(22) Filed: May 24, 2005

(65) Prior Publication Data

US 2006/0054168 A1    Mar. 16, 2006

(30) Foreign Application Priority Data

Sep. 10, 2004   (TW) .............................. 93214427 U

(51) Int. Cl.
*A62B 18/08* (2006.01)
(52) U.S. Cl. .................... 128/206.29; 128/206.28; 128/206.24; 128/206.26; 128/206.21; 128/201.26
(58) Field of Classification Search ........... 128/206.29, 128/206.28, 206.24, 206.26, 206.21, 201.26
See application file for complete search history.

(56) References Cited

U.S. PATENT DOCUMENTS

| | | | | |
|---|---|---|---|---|
| 1,175,799 A | * | 3/1916 | McGargill | 128/206.11 |
| 1,362,766 A | * | 12/1920 | McGargill | 128/205.27 |
| 1,395,948 A | * | 11/1921 | Drager | 128/206.29 |
| 1,632,766 A | * | 6/1927 | Von Uffel | 252/301.36 |
| 1,978,994 A | * | 10/1934 | Fortunato | 128/201.16 |
| 2,383,649 A | * | 8/1945 | Heidbrink | 128/205.25 |
| 3,602,219 A | * | 8/1971 | Warncke | 128/201.15 |
| 3,809,079 A | * | 5/1974 | Buttaravoli | 128/206.24 |
| 4,029,092 A | * | 6/1977 | Morgan | 128/201.11 |
| 4,470,413 A | * | 9/1984 | Warncke | 128/201.18 |
| 4,573,463 A | * | 3/1986 | Hall | 128/205.24 |
| 4,655,213 A | * | 4/1987 | Rapoport et al. | 128/205.25 |
| 4,890,609 A | * | 1/1990 | Wilson, II | 128/206.29 |
| 5,954,048 A | * | 9/1999 | Thornton | 128/201.18 |
| 6,016,802 A | * | 1/2000 | Jackson | 128/205.25 |
| 6,584,975 B1 | * | 7/2003 | Taylor | 128/206.11 |
| 6,758,212 B1 | * | 7/2004 | Swann | 128/201.25 |
| 6,763,831 B1 | * | 7/2004 | Sniadach | 128/206.29 |
| 6,860,270 B1 | * | 3/2005 | Sniadach | 128/207.14 |

* cited by examiner

*Primary Examiner*—Henry Bennett
*Assistant Examiner*—Nihir Patel
(74) *Attorney, Agent, or Firm*—Thomas, Kayden, Horstemeyer & Risley

(57) ABSTRACT

A face mask for use in gas delivery applications, such as breathable gas or aerosol drug systems. The face mask includes a body having a peripheral edge for placement against the face of a wearer. The peripheral edge defines a single chamber over the nose and the mouth of the wearer. An inlet opening is formed on a surface of the body for supplying inhalation gas to the nose through the chamber. A vent assembly inwardly extends from the surface of the body to the chamber and seals around the mouth for passing exhalation gas to the exterior of the body.

5 Claims, 3 Drawing Sheets

FACE MASK

BACKGROUND OF THE INVENTION

The invention relates to the field of face masks. More particularly, the invention relates to the field of face masks for use in gas delivery applications.

In traditional face mask design, breathable gas or aerosol drug is directly delivered into a chamber of the face mask, while at the same time, the exhalation gas generated from the nose or the mouth of the wearers will enter into the chamber. Therefore, the substantial amount of the breathable gas or aerosol drug to be inhaled by the wearer is not enough since the concentration of the breathable gas or aerosol drug is diluted with the exhalation gas.

SUMMARY OF THE INVENTION

An exemplary embodiment of the present invention overcomes the above-described problems by providing face masks that could directly pass exhalation gas to the exterior of body thereof.

An exemplary embodiment of the invention provides a face mask for use in gas delivery applications, such as breathable gas or aerosol drug systems. The face mask includes a body having a peripheral edge for placement against the face of a wearer. The peripheral edge defines a single chamber over the nose and the mouth of the wearer. An inlet opening is formed on a surface of the body for supplying inhalation gas to the nose through the chamber. A vent assembly inwardly extends from the surface of the body to the chamber and seals around the mouth for passing exhalation gas to the exterior of the body.

BRIEF DESCRIPTION OF THE DRAWINGS

The present invention will be described by way of exemplary embodiments, but not limitations, illustrated in the accompanying drawings in which like references denote similar elements, and in which.

DETAILED DESCRIPTION OF THE INVENTION

Various aspects of the system and method of the present invention will be described, and for purposes of explanation, specific configurations and details are set forth in order to provide a thorough understanding of the present invention. However, it will be apparent to one skilled in the art that the present invention may be practiced without these specific details. Furthermore, well known features have been omitted or simplified in order to prevent obscuring the present invention.

Figure 1:
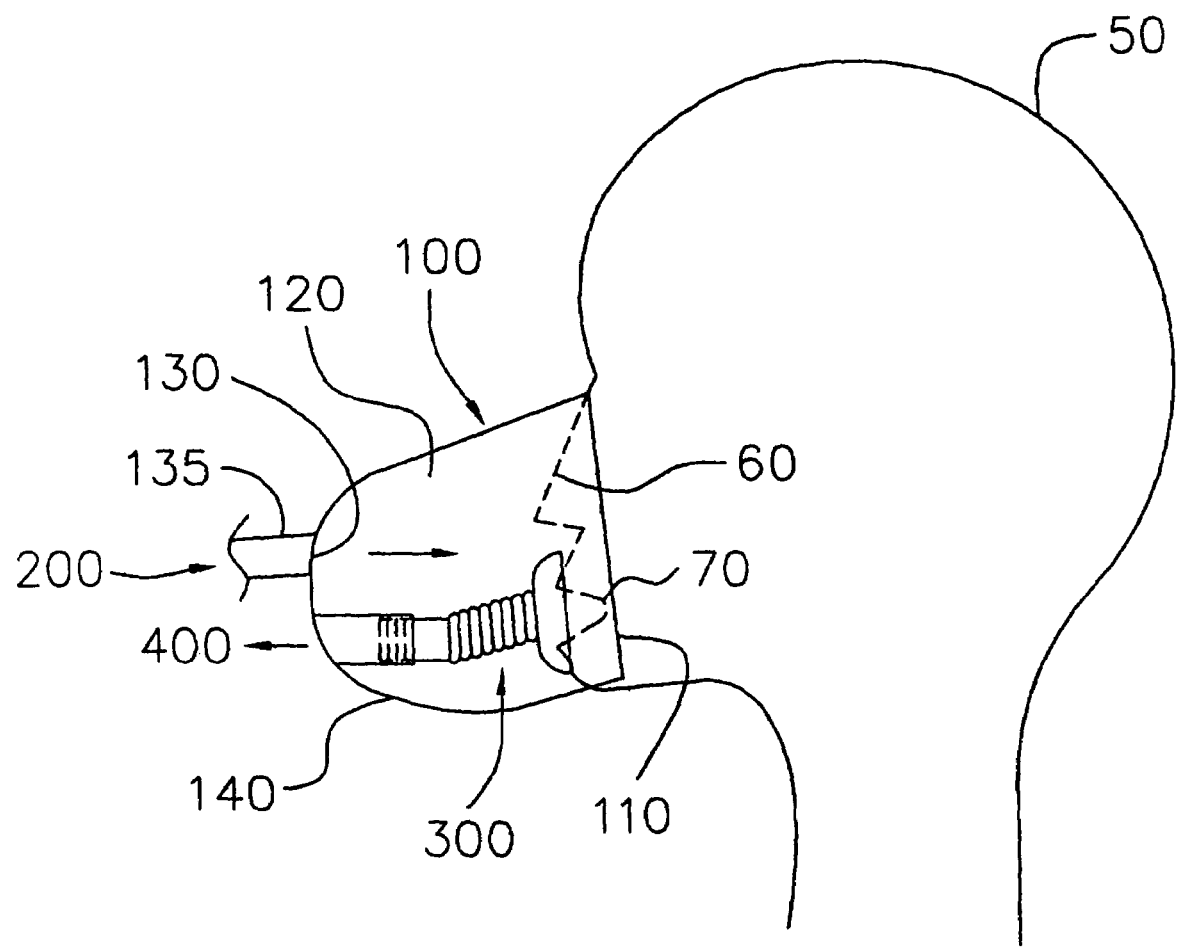
FIG. 1 illustrates a side view of the nose and the mouth of a wearer covered by a face mask according to an exemplary embodiment of the present invention.

FIG. 1 illustrates the face of a wearer 50 such as a person or a patient, and the nose 60 and the mouth 70 covered by a face mask 10, according to an exemplary embodiment of the present invention. A body 100 of the face mask 10 includes a peripheral edge 110 for placement against the face. The peripheral edge 110 of the body defines a single chamber 120 over the nose 60 and the mouth 70 of the wearer. The body 100 is typically made of a flexible material, such as a thermoplastic, e.g., PVC material. For example, the face mask 10 is generally of a relatively thin material with the peripheral edge 110 also being of a thin flexible construction so that it can flexibly engage the face of the wearer.

An inlet opening 130 communicated with a gas delivering system through a pipe 135 is formed on a surface 140 of the body 100 for supplying inhalation gas 200 to the nose 60 through the chamber 120.

A vent assembly 300 inwardly extends from the surface 140 of the body 100 to the chamber 120 and seals around the mouth 70 for passing exhalation gas 400 to the exterior of the body 100. Preferably, the length of the vent assembly 300 may be adjustable to match the position of the mouth 70.

Figure 2:
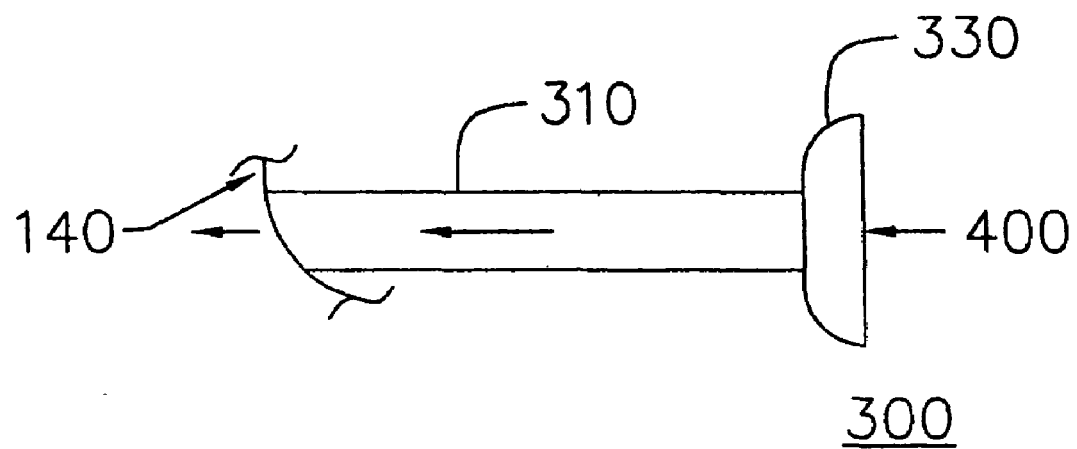
FIG. 2 illustrates a perspective view of a face mask according to an exemplary embodiment of the present invention.

Referring to FIG. 2, in an exemplary embodiment of the invention, the vent assembly 300 preferably includes a vent pipe 310 for passing exhalation gas 400 to the exterior of the body 100. Typically, the vent pipe 310 may be made of flexible plastic material.

In one example, the vent assembly 300 further includes a hollow contact portion 330 communicated with the vent pipe 310. In general, the hollow contact portion 330 is adapted to seal around the mouth for passing exhalation gas 400 to the exterior of the surface 140.

Figure 3:
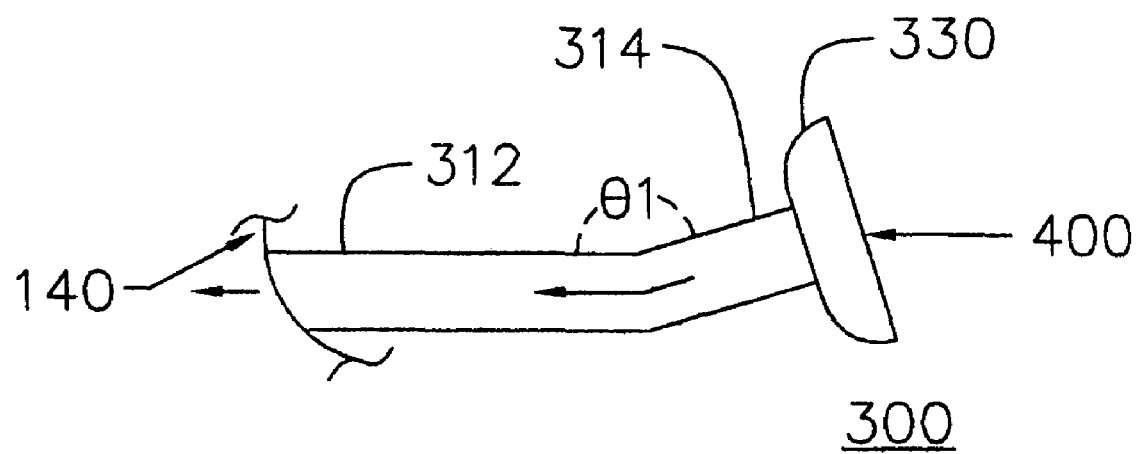
FIG. 3 illustrates a perspective view of a face mask according to an exemplary embodiment of the present invention.

Referring to FIG. 3, in an exemplary embodiment of the invention, the vent assembly 300 preferably includes a first pipe 312 communicated with a second pipe 314 in a predetermined angle $\theta 1$. Typically, the second pipe 314 is to be aligned with the mouth 70 by the angle of $\theta 1$. In one example, a hollow contact portion 330 may be communicated with the second pipe 314 for sealing around the mouth.

Figure 4:
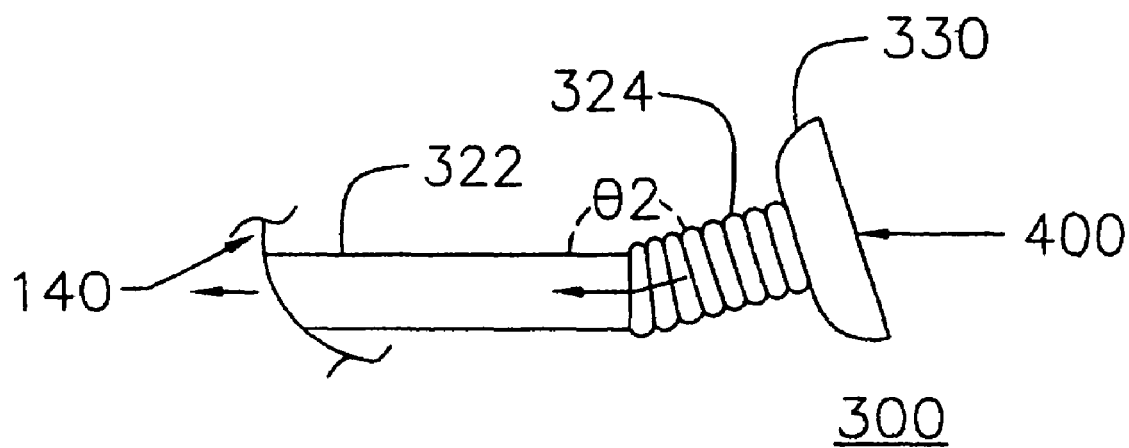
FIG. 4 illustrates a perspective view of a face mask according to an exemplary embodiment of the present invention.

Referring to FIG. 4, in an exemplary embodiment of the invention, the vent assembly 300 preferably includes a deformable member 324 communicated with a vent pipe 322. Typically, the deformable member 324 is bendable to align with the mouth 70 by an angle of $\theta 2$. In one example, a hollow contact portion 330 may be communicated with the deformable member 324 for sealing around the mouth.

Figure 5:
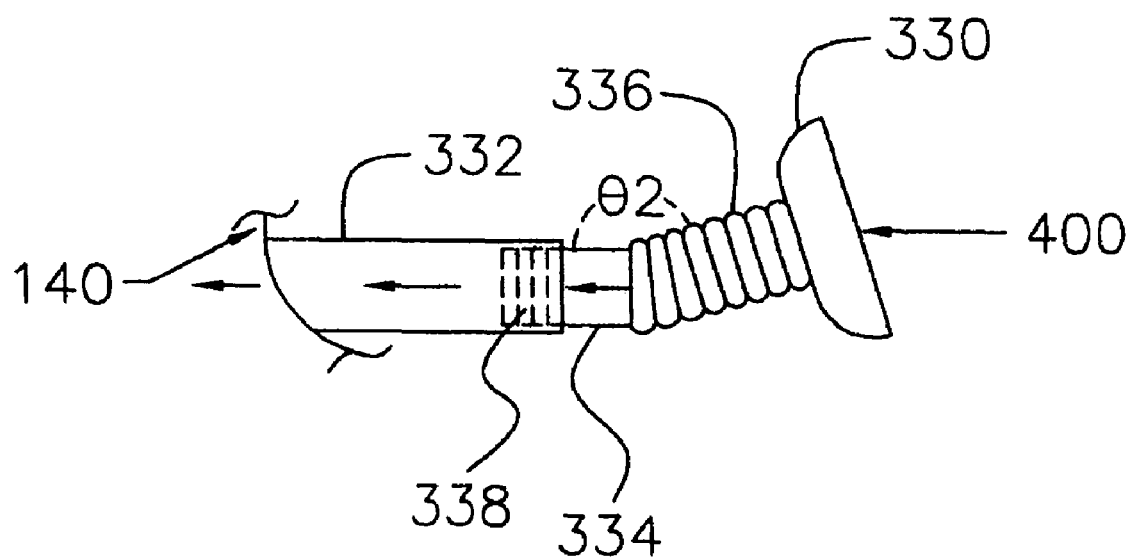
FIG. 5 illustrates a perspective view of a face mask according to an exemplary embodiment of the present invention.

Referring to FIG. 5, in an exemplary embodiment of the invention, a detachable vent assembly includes a first vent pipe 332, a second vent pipe 334 and a deformable member 336. Typically, the first vent pipe 332 may inwardly extend from the surface 140 of the body 100 to the chamber 120. Preferably, the second vent pipe 334 is connected to the first vent pipe 332 in a detachable form.

In one example, the deformable member 336 may be communicated with the second vent pipe 334 in a predetermined angle of $\theta 2$. Typically, the deformable member 336 is bendable to align with the mouth. A hollow contact portion 330 may be communicated with the deformable member 336 for sealing around the mouth. Preferably, the length of the deformable member 336 may be adjustable to match the position of the mouth 70.

In one example, the second vent pipe 334 includes a connection portion 338 being inserted into the first vent pipe 332 in a detachable form.

In the above-described embodiments, breathable gas or aerosol drug may be directly delivered into the chamber 120 of the face mask 10, while at the same time, the exhalation gas 400 generated from the nose 60 or mouth 70 of the wearers may be directly passed to the exterior of the face mask 10. Therefore, the substantial amount of the breathable gas or aerosol drug to be inhaled by the wearer is enough since the concentration of the breathable gas or aerosol drug is not diluted with the exhalation gas.

In yet another example shown in FIG. 5, the used second vent pipe 336 with the hollow contact portion 330 contacting the nose or the mouth may be replaced by a new one. Therefore, the face mask may be reused due to the use of the detachable vent assembly.

While the invention has been described by way of example and in terms of the preferred embodiments, it is to be understood that the invention is not limited to the disclosed embodiments. To the contrary, it is intended to cover various modifications and similar arrangements as would be apparent to those skilled in the art. Therefore, the scope of the appended claims should be accorded the broadest interpretation so as to encompass all such modifications and similar arrangements.

What is claimed is:

1. A face mask, comprising:
   a body having a peripheral edge for placement against a face of a wearer, the peripheral edge defining a chamber over the nose and the mouth of the wearer;
   an inlet opening, formed on a surface of the body for supplying inhalation gas to the nose through the chamber;
   a vent assembly, inwardly extending from the surface of the body to the chamber, wherein the vent assembly comprises:
   a vent pipe for passing exhalation gas to the exterior of the body;
   a deformable member communicated with the vent pipe, being bendable to align with the mouth; and
   a hollow contact portion communicated with the deformable member, being adapted to seal around the mouth.

2. A face mask, comprising:
   a body having a peripheral edge for placement against a face of a wearer, the peripheral edge defining a chamber over the nose and the mouth of the wearer;
   an inlet opening, formed on a surface of the body for supplying inhalation gas to the nose through the chamber;
   a first vent pipe, inwardly extending from the surface of the body to the chamber;
   a second vent pipe, connected to the first vent pipe in a detachable form;
   a deformable member communicated with the second vent pipe, the deformable member is bendable to align with the mouth; and
   a hollow contact portion communicated with the deformable member, the hollow contact portion is adapted to seal around the mouth.

3. The face mask as recited in claim 2 wherein the second vent pipe comprises a connection portion inserted into the first vent pipe in a detachable form.

4. The face mask as recited in claim 1 wherein the length of the deformable member is adjustable to match the position of the mouth.

5. The face mask as recited in claim 2 wherein the length of the deformable member is adjustable to match the position of the mouth.

* * * * *